(12) United States Patent
Koller et al.

(10) Patent No.: US 8,759,581 B2
(45) Date of Patent: Jun. 24, 2014

(54) METHOD OF PREPARING 1-CHLOROACETAMIDO-1,3,3,5,5-PENTAMETHYLCYCLOHEXANE

(75) Inventors: Herbert Koller, Vienna (AT); Michael Pyerin, Brunn am Gebirge (AT)

(73) Assignee: Merz Pharma GmbH & Co. KGaA, Frankfurt am Main (DE)

( * ) Notice: Subject to any disclaimer, the term of this patent is extended or adjusted under 35 U.S.C. 154(b) by 187 days.

(21) Appl. No.: 13/379,449

(22) PCT Filed: Jun. 28, 2010

(86) PCT No.: PCT/EP2010/003920
§ 371 (c)(1),
(2), (4) Date: Jan. 31, 2012

(87) PCT Pub. No.: WO2011/000537
PCT Pub. Date: Jan. 6, 2011

(65) Prior Publication Data
US 2012/0130127 A1    May 24, 2012

Related U.S. Application Data

(60) Provisional application No. 61/269,769, filed on Jun. 29, 2009.

(30) Foreign Application Priority Data

Jun. 29, 2009  (EP) ..................................... 09008462

(51) Int. Cl.
*C07C 231/06*   (2006.01)
*C07C 211/35*   (2006.01)

(52) U.S. Cl.
USPC .......................................... 564/129; 564/462

(58) Field of Classification Search
USPC ................................................ 564/129, 462
See application file for complete search history.

(56) References Cited

U.S. PATENT DOCUMENTS

| 4,126,140 A | 11/1978 | Light et al. |
| 2009/0082596 A1 | 3/2009 | Schickaneder |
| 2009/0137826 A1 | 5/2009 | Guminski et al. |
| 2009/0170908 A1 | 7/2009 | Shimada et al. |
| 2012/0116125 A1 | 5/2012 | Koller et al. |
| 2012/0123166 A1 | 5/2012 | Koller et al. |
| 2012/0130130 A1 | 5/2012 | Koller et al. |
| 2012/0130131 A1 | 5/2012 | Koller et al. |

FOREIGN PATENT DOCUMENTS

| JP | 1967-010499 | 7/1967 |
| JP | 2007-308480 | 11/2007 |
| JP | 2007-308483 | 11/2007 |
| WO | WO 99/01416 | 1/1999 |

OTHER PUBLICATIONS

U.S. Appl. No. 13/376,773, Koller, et al.
Bell, et al., J. Am. Chem. Soc., 1981, 103, 1163-1171.
Dean, et al., J. Chem. Soc. Perkin Trans. 2, 1991, 10, 1541-1543.
International Search Report and Written Opinion for PCT/EP2010/003919 dated Sep. 2, 2010.
International Search Report and Written Opinion for PCT/EP2010/003921 dated Oct. 27, 2010.
International Search Report and Written Opinion for PCT/EP2010/003922 dated Oct. 27, 2010.
International Search Report and Written Opinion for PCT/EP2010/003923 dated Sep. 2, 2010.
International Search Report and Written Opinion for PCT/EP2010/003924 dated Oct. 27, 2010.
Jirgensons, et al., Eur. J. Med. Chem., 2000, 35,555-565.
Kharasch, et al., J. Am. Chem. Soc., 1941, 93, 2308-2316.
Chiurdoglu, G.M.A., Bull Soc Chim Belg, 1954, vol. 63, p. 357-378.
International search report / Written Opinion for PCT/EP2010/003920 of Oct. 15, 2010.
Jirgensons et al, Synthesis, 2000, p. 1709-1712.
W. Danysz et al., Currrent Pharmaceutical Design, 2002, vol. 8, p. 835-843.

*Primary Examiner* — Shailendra Kumar
(74) *Attorney, Agent, or Firm* — Hueschen and Sage

(57) ABSTRACT

Method of preparing 1-chloroacetamido-1,3,3,5,5-pentamethylcyclohexane, an intermediate in the synthesis of 1-amino-1,3,3,5,5-pentamethylcyclohexane (Neramexane) or a pharmaceutically acceptable salt thereof, comprising step (iii):
(iii) reacting 1-hydroxy-1,3,3,5,5-pentamethylcyclohexane with chloroacetonitrile in the presence of an acid,
wherein 1-hydroxy-1,3,3,5,5-pentamethylcyclohexane is employed in step (iii) as obtained in the reaction of a methylmagnesium halide with 3,3,5,5-tetramethylcyclohexanone without having been subjected to a purification step.

19 Claims, No Drawings

METHOD OF PREPARING 1-CHLOROACETAMIDO-1,3,3,5,5-PENTAMETHYLCYCLOHEXANE

This application is a 371 of PCT/EP2010/003920, filed Jun. 28, 2010, which claims benefit of 61/269,769 Jun. 29, 2009.

FIELD OF THE INVENTION

This invention relates to a method of preparing 1-chloroacetamido-1,3,3,5,5-pentamethylcyclohexane. This compound is an intermediate within the preparation of 1-amino-1,3,3,5,5-pentamethylcyclohexane (Neramexane) or a pharmaceutically acceptable salt thereof.

BACKGROUND OF THE INVENTION 1-amino-1,3,3,5,5-pentamethylcyclohexane (Neramexane) and pharmaceutically acceptable salts thereof are valuable agents for the continuous therapy of patients suffering from diseases and conditions such as tinnitus, and nystagmus.

Methods of preparing these agents are known.

In one method, commercially available isophorone is converted to Neramexane in a reaction sequence comprising five steps according to the following reaction scheme (W. Danysz et al., Current Pharmaceutical Design, 2002, 8, 835-843):

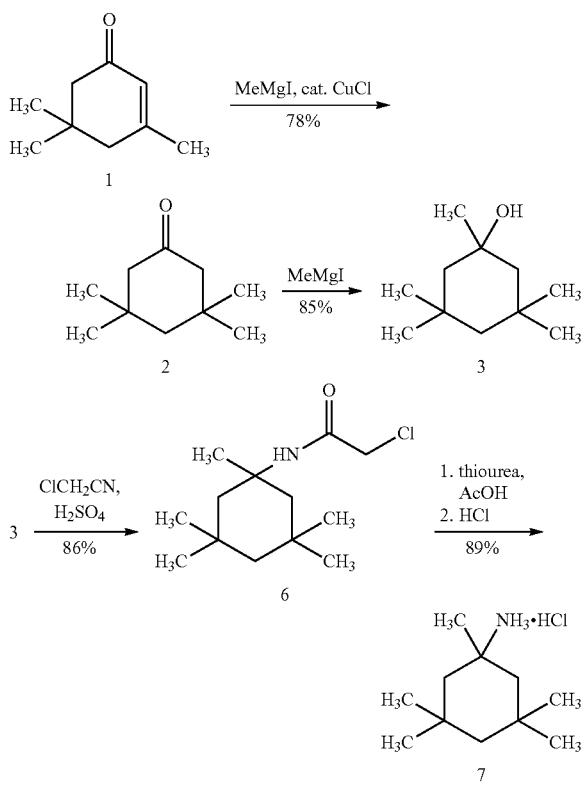

In the first step of the sequence (step (i)), isophorone 1 is converted to 3,3,5,5-tetramethylcyclohexanone 2 by CuCl-catalyzed conjugate addition of methyl-magnesium iodide.

In the second step (step (ii)), 3,3,5,5-tetramethylcyclohexanon 2 is converted to 1,3,3,5,5-pentamethylcyclohexanol 3 by Grignard reaction with methylmagnesium iodide.

Danysz discloses that compound 3 has been prepared according to the method of reference [4] (Chiurdoglu). This reference discloses the reaction of 3,3,5,5-tetramethylcyclohexanone with methylmagnesium bromide to the respective cyclohexanol. Page 377, section 5 discloses that compound 3 has been subjected to distillation (boiling point 91 to 92° C. at 22 torr), i.e. it has been purified. Accordingly, compound 3 as used by Danysz is purified.

In the third step (step (iii)), said cyclohexanol 3 is converted to 1-chloroacetamido-1,3,3,5,5-pentamethylcyclohexane 6 by chloroacetonitrile in a Ritter reaction.

Danysz discloses that compound 6 has been prepared according to the method of reference [6] (Jirgensons). This reference discloses the Ritter reaction of the cyclohexanol with chloroacetonitrile to the respective amide (Scheme on page 1709, compound 1a, compound 2a). According to the general reaction procedure, the resulting amide is subjected to a Kugelrohr short path distillation, i.e. it has been subjected to a purification step (page 1710, right column, first and second paragraph). Accordingly, compound 6 as used by Danysz is purified.

In the fourth step (step (iv)), subsequent cleavage of the chloroacetamido group in amide 6 with thiourea, and acidification of the resulting amine with hydrochloric acid in the fifth step (step (v)) of the reaction sequence results in Neramexane (1-amino-1,3,3,5,5-pentamethylcyclohexane) 7 in the form of its hydrochloride.

OBJECTS OF THE INVENTION

One object of the invention is to improve one or more of the individual reaction steps of the above referenced reaction sequence in order to provide a method of preparing 1-amino-1,3,3,5,5-pentamethylcyclohexane or a pharmaceutically acceptable salt thereof that allows an advantageous realization on an economical industrial scale. It is in another object to minimize the amount of waste and/or unused chemicals produced during the manufacture of Neramexane or a pharmaceutically acceptable salt thereof. It is a further object to optimize or improve the yield and/or selectivity and/or product quality in regard to Neramexane or a pharmaceutically acceptable salt thereof. Particularly, the subject application aims to improve above step (iii), i.e. the reaction of 1-hydroxy-1,3,3,5,5-pentamethylcyclohexane with chloroacetonitrile. Such an improved method may be regarded as one prerequisite for an advantageous manufacture of Neramexane or a pharmaceutically acceptable salt thereof on an economical industrial scale.

SUMMARY OF THE INVENTION

The present invention relates to a method of preparing 1-chloroacetamido-1,3,3,5,5-pentamethylcyclohexane comprising step (iii):

(iii) reacting 1-hydroxy-1,3,3,5,5-pentamethylcyclohexane with chloroacetonitrile in the presence of an acid, wherein 1-hydroxy-1,3,3,5,5-pentamethylcyclohexane is reacted in step (iii) as obtained in the reaction of a methylmagnesium halide with 3,3,5,5-tetramethylcyclohexanone without having been subjected to a purification step.

In one embodiment, the method comprises prior to step (iii) step (ii):

(ii) converting 3,3,5,5-tetramethylcyclohexanone to 1-hydroxy-1,3,3,5,5-pentamethylcyclohexane in the presence of a methylmagnesium halide.

In one embodiment, said methylmagnesium halide is the chloride.

In one embodiment, the non-purified 1-hydroxy-1,3,3,5,5-pentamethylcyclohexane comprises 1-hydroxy-1,3,3,5,5-pentamethylcyclohexane in an amount ranging from 85 to 98% by weight.

In one embodiment, said acid is selected from the group consisting of sulphuric acid, nitric acid, phosphorus acid, acetic acid, or mixtures thereof.

In one embodiment, sulphuric acid is added to a mixture of 1-hydroxy-1,3,3,5,5-pentamethylcyclohexane, chloroacetonitrile and acetic acid.

In one embodiment, 1-hydroxy-1,3,3,5,5-pentamethylcyclohexane and acetic acid are provided in a weight ratio of 1:1.5 to 1:2.5; and, per molar equivalent 1-hydroxy-1,3,3,5,5-pentamethylcyclohexane, 1.5 to 2.5 molar equivalents chloroacetonitrile and 2.5 to 3.5 molar equivalents sulphuric acid are employed.

In one embodiment, the temperature in step (iii) is kept in a range of from 0° C. to 30° C.

In one embodiment, the 1-chloroacetamido-1,3,3,5,5-pentamethylcyclohexane as obtained in step (iii) is not subjected to a purification step.

In another aspect, the invention also relates to a method of preparing 1-amino-1,3,3,5,5-pentamethylcyclohexane or a pharmaceutically acceptable salt thereof, comprising step (iii):
(iii) reacting 1-hydroxy-1,3,3,5,5-pentamethylcyclohexane with chloroacetonitrile in the presence of an acid,
wherein 1-hydroxy-1,3,3,5,5-pentamethylcyclohexane is reacted in step (iii) as obtained in the reaction of a methylmagnesium halide with 3,3,5,5-tetramethylcyclohexanone without having been subjected to a purification step.

Within said method of preparing 1-amino-1,3,3,5,5-pentamethylcyclohexane, step (iii) may be performed according to any one of the embodiments as defined above, either alone or in combination.

It has been unexpectedly discovered that by employing in step (iii) 1-hydroxy-1,3,3,5,5-pentamethylcyclohexane as obtained in the reaction of a methylmagnesium halide with 3,3,5,5-tetramethylcyclohexanone without having been subjected to a purification step, results in a high yield of crude 1-chloroacetamido-1,3,3,5,5-pentamethylcyclohexane, the yield ranging from 90 to 100% by weight. Since the method according to the invention allows the omission of complex cleaning steps of the intermediate such as distillation or recrystallization or chromatography, which commonly result in product loss, and since the target compound may also be employed in a non-purified form in the next reaction step (iv) of the sequence of preparing Neramexane or a pharmaceutically acceptable salt thereof as referenced in the Background section, the novel simplified method may be performed on an advantageous economical industrial scale.

DETAILED DESCRIPTION OF THE INVENTION

This invention relates to a method of preparing 1-chloroacetamido-1,3,3,5,5-pentamethylcyclohexane.

Specifically, this invention relates to a method of preparing 1-chloroacetamido-1,3,3,5,5-pentamethylcyclohexane comprising step (iii):
(iii) reacting 1-hydroxy-1,3,3,5,5-pentamethylcyclohexane with chloroacetonitrile in the presence of an acid,
wherein 1-hydroxy-1,3,3,5,5-pentamethylcyclohexane is reacted in step (iii) as obtained in the reaction of a methylmagnesium halide with 3,3,5,5-tetramethylcyclohexanone without having been subjected to a purification step.

Accordingly, the method of the invention includes that the 1-hydroxy-1,3,3,5,5-pentamethylcyclohexane is reacted in step (iii) as it has been obtained in the previous reaction of a methylmagnesium halide with 3,3,5,5-tetramethylcyclohexanone without having been subjected to a purification in a purification step. The form of 1-hydroxy-1,3,3,5,5-pentamethylcyclohexane as used as a starting material in step (iii) is sometimes also referred to herein as "non-purified form".

The term "without having been subjected to a purification step" excludes the recrystallization, distillation, or chromatography, or combinations thereof, of the compound 1-hydroxy-1,3,3,5,5-pentamethylcyclohexane itself.

The term "without having been subjected to a purification step" allows standard work up steps such as the removal of a solvent from a mixture comprising 1-hydroxy-1,3,3,5,5-pentamethylcyclohexane, and said solvent by distillation, or the extraction of 1-hydroxy-1,3,3,5,5-pentamethylcyclohexane from an aqueous phase by means of a solvent, or the drying of a mixture comprising 1-hydroxy-1,3,3,5,5-pentamethylcyclohexane and a solvent using e.g. anhydrous sodium sulphate, the drying of 1-hydroxy-1,3,3,5,5-pentamethylcyclohexane in vacuo, the washing of 1-hydroxy-1,3,3,5,5-pentamethylcyclohexane with a liquid, and the like.

Purification by "recrystallization", "distillation", or "chromatography" are the classical methods employed for purifying chemical compounds such as organic compounds both on a laboratory and an industrial scale.

Recrystallization is a method of separating mixtures based on differences of the compounds contained therein in their solubilities in a solvent or a mixture of solvents. If a compound is to be purified by recrystallization, it is dissolved in an appropriate solvent, which is then allowed to cool. This results in the desired purified compound dropping (recrystallization) from the solution. However, it is also possible to add to the solution another solvent, in which the desired compound is insoluble until the desired compounds begins to precipitate. Accordingly, in the meaning of the present invention, the term "recrystallization" means that a compound is transferred to a dissolved condition and precipitates or is precipitated from said dissolved condition to form the purified product.

Distillation is a method of separating mixtures based on differences of the compounds contained therein in their volatilities in a boiling liquid mixture. Accordingly, in the meaning of the present invention, the term "distillation" as mentioned in the definition of the term "purification" means that in order to be "distilled" a compound (here: 1-hydroxy-1,3,3,5,5-pentamethylcyclohexane) has to be transferred from the liquid phase to the vapour phase and is subsequently condensed to form the purified compound.

Chromatography in chemistry is a method of separating mixtures based on differences in the distribution of the compounds contained therein between a stationary phase and a mobile phase. A typical method is column chromatography which may be used for preparative applications.

Thus, 1-hydroxy-1,3,3,5,5-pentamethylcyclohexane is not subjected to a purification step selected from recrystallization, distillation, or chromatography.

At ambient temperature, 1-hydroxy-1,3,3,5,5-pentamethylcyclohexane as obtained in the reaction of a methylmagnesium halide and 3,3,5,5-tetramethylcyclohexanone and employed in step (iii) is a liquid. In one embodiment, said compound is not distilled, i.e. it is not subjected to distillation. This means that 1-hydroxy-1,3,3,5,5-pentamethylcyclohexane is not transferred from the liquid phase to the vapour phase and is subsequently condensed to form the purified compound.

In one embodiment, the liquid 1-hydroxy-1,3,3,5,5-pentamethylcyclohexane is not subjected to chromatography.

This means that 1-hydroxy-1,3,3,5,5-pentamethylcyclohexane is not distributed between a mobile and a stationary phase to form the purified product.

In one embodiment, the liquid 1-hydroxy-1,3,3,5,5-pentamethylcyclohexane is not transferred to a dissolved condition and is not precipitated from said dissolved condition to form the purified product.

Accordingly, the invention relates to a method of preparing 1-chloroacetamido-1,3,3,5,5-pentamethylcyclohexane comprising step (iii):
(iii) reacting 1-hydroxy-1,3,3,5,5-pentamethylcyclohexane with chloroacetonitrile in the presence of an acid,
wherein 1-hydroxy-1,3,3,5,5-pentamethylcyclohexane is obtained as a liquid in the reaction of a methylmagnesium halide with 3,3,5,5-tetramethylcyclohexanone, wherein the liquid is not subjected to a purification step of distillation or to a purification step of chromatography or to a purification step of recrystallization.

In one embodiment, 1-hydroxy-1,3,3,5,5-pentamethylcyclohexane is prepared by reaction of a methylmagnesium halide with 3,3,5,5-tetramethylcyclohexanone (step (ii)) and is not subjected to a purification step.

In one embodiment, 1-hydroxy-1,3,3,5,5-pentamethylcyclohexane may be prepared according to the method as referenced in the Background section (step (ii)), i.e. by reaction of 3,3,5,5-tetramethylcyclohexanone with methylmagnesium iodide.

However, in other embodiments, as methylmagnesium halide, the bromide or chloride may be used.

In one embodiment, said methylmagnesium halide is methylmagnesium chloride.

In one embodiment, a solution of 3,3,5,5-tetramethylcyclohexanone in tetrahydrofurane is added to a solution of methylmagnesium chloride in tetrahydrofurane in order to prepare 1-hydroxy-1,3,3,5,5-pentamethylcyclohexane.

In one embodiment, about 1.2 to 1.75 molar equivalents methylmagnesium chloride are employed per molar equivalent 3,3,5,5-tetramethylcyclohexanone.

In one embodiment, the reaction of the Grignard reagent with 3,3,5,5-tetramethylcyclohexanone is performed such that the temperature is controlled.

In one embodiment, the reaction is performed such that the temperature is maintained in a relatively narrow temperature range.

In one embodiment, the reaction according to step (ii) is performed at a temperature of from −5° C. to 30° C., or 0° C. to 30° C., or 0° C. to 25° C., or 0° C. to 20° C., or 5° C. to 20° C., or 10° C. to 25° C., or 15° C. to 25° C.

After the reaction of 3,3,5,5-tetramethylcyclohexane with the Grignard reagent, the reaction mixture may be treated with water to destroy an excess of Grignard reagent, if any employed, respectively to destroy basic magnesium compounds, in order to isolate 1-hydroxy-1,3,3,5,5-pentamethylcyclohexane.

In one embodiment, an acid such as hydrochloric acid or an ammonium salt is added to support the formation of 1-hydroxy-1,3,3,5,5-pentamethylcyclohexane.

In one embodiment, the product formed in step (ii) is obtained and isolated by extracting the aqueous mixture with an appropriate organic solvent such as methylene chloride or toluene or petroleum ether. Subsequent to the extracting, the solvent is removed by distillation. The residue comprising crude 1-hydroxy-1,3,3,5,5-pentamethylcyclohexane as obtained and isolated is employed without subjecting the crude product to a purification step, e.g. distillation or chromatography, in step (iii) of the method of the invention.

In another embodiment, subsequent to the extracting, the extract may be dried according to known methods. For example, the extract may be dried over sodium sulphate. After separating off said sulphate by filtration, the solvent may be removed by distillation. The residue comprising crude 1-hydroxy-1,3,3,5,5-pentamethylcyclohexane as obtained and isolated is employed without subjecting the crude product to a purification step, e.g. distillation or chromatography, in step (iii) of the method of the invention.

In one embodiment, the yield of crude 1-hydroxy-1,3,3,5,5-pentamethylcyclohexane ranges from 90% to 100% by weight.

In one embodiment, the crude product comprises 1-hydroxy-1,3,3,5,5-pentamethylcyclohexane in an amount of from 85 to 98% by weight as may be determined by gas-liquid chromatography.

In one embodiment, the crude product contains 1-hydroxy-1,3,3,5,5-pentamethylcyclohexane in an amount of from 94 to 98% by weight.

The conversion of 1-hydroxy-1,3,3,5,5-pentamethylcyclohexane to 1-chloroacetamido-1,3,3,5,5-pentamethylcyclohexane in step (iii) is effected by means of the reaction of 1-hydroxy-1,3,3,5,5-pentamethylcyclohexane with chloroacetonitrile in the presence of an acid in a Ritter reaction.

In one embodiment, the Ritter reaction according to step (iii) may be performed according to the method as referenced in the prior art.

In one embodiment, said acid is selected from the group consisting of sulphuric acid, nitric acid, phosphorus acid, acetic acid, or mixtures thereof.

In one embodiment, the acids are employed as concentrated acids.

In one embodiment, sulphuric acid and acetic acid are employed. In one embodiment, sulphuric acid is concentrated sulphuric acid, and acetic acid is glacial acetic acid.

In one embodiment, 1-hydroxy-1,3,3,5,5-pentamethylcyclohexane as obtained and isolated in step (ii) is provided in acetic acid, and a mixture of chloroacetonitrile and sulphuric acid is added to said mixture.

In another embodiment, 1-hydroxy-1,3,3,5,5-pentamethylcyclohexane as obtained and isolated in step (ii) and chloroacetonitrile are provided in acetic acid, and sulphuric acid is added to said mixture.

In one embodiment, 1-hydroxy-1,3,3,5,5-pentamethylcyclohexane and acetic acid are provided in a weight ratio of 1:1.5 to 1:2.5. In one embodiment, the weight ratio is 1:2.

In one embodiment, from 1.5 to 2.5 molar equivalents chloroacetonitrile and from 2.5 to 3.5 molar equivalents sulphuric acid are employed per molar equivalent 1-hydroxy-1,3,3,5,5-pentamethylcyclohexane.

In one embodiment, 1-hydroxy-1,3,3,5,5-pentamethylcyclohexane and acetic acid are provided in a weight ratio of, per molar equivalent 1-hydroxy-1,3,3,5,5-pentamethylcyclohexane, from 1:1.5 to 1:2.5, and from 1.5 to 2.5 molar equivalents chloroacetonitrile and from 2.5 to 3.5 molar equivalents sulphuric acid are employed.

In another embodiment, about 2 molar equivalents chloroacetonitrile and 3 molar equivalents sulphuric acid are employed.

In one embodiment, 1-hydroxy-1,3,3,5,5-pentamethylcyclohexane and acetic acid are provided in a weight ratio of from 1:2, and, per molar equivalent 1-hydroxy-1,3,3,5,5-pentamethylcyclohexane, 2 molar equivalents chloroacetonitrile and 3 molar equivalents sulphuric acid are employed.

In one embodiment, the addition of sulphuric acid or the addition of the mixture of chloroacetonitrile and sulphuric acid is performed such that the reaction temperature is kept in a range of from 0° C. to 30° C., or 0° C. to 20° C., or 0° C. to 15° C., or 5° C. to 10° C.

In general, the reaction proceeds relatively fast towards the target compound 1-chloroacetamido-1,3,3,5,5-pentamethylcyclohexane. In one embodiment, the reaction may be terminated after 2 hours, or even one hour.

After the termination of the reaction, the reaction mixture may be poured into water or ice or a mixture of water and ice in order to work up the mixture. The precipitating 1-chloroacetamido-1,3,3,5,5-pentamethylcyclohexane may be isolated by filtration.

The precipitate may be washed with water.

In one embodiment, the yield of crude product 1-chloroacetamido-1,3,3,5,5-pentamethylcyclohexane is in the range of from 90 to 100%, or from 94 to 100%, or from 98 to 100% by weight.

In one embodiment, 1-chloroacetamido-1,3,3,5,5-pentamethylcyclohexane as obtained in step (iii) is not further purified, i.e. is not subjected to a purification step.

At ambient temperature, 1-chloroacetamido-1,3,3,5,5-pentamethylcyclohexane as obtained in step (iii) is a solid. In one embodiment, said compound is not recrystallized.

In another embodiment, 1-chloroacetamido-1,3,3,5,5-pentamethylcyclohexane is not subjected to chromatography.

It may be employed as the crude product in step (iv) for the conversion to 1-amino-1,3,3,5,5-pentamethylcyclohexane or a pharmaceutically acceptable salt thereof of the reaction sequence as referenced in the Background section.

Accordingly, 1-chloroacetamido-1,3,3,5,5-pentamethylcyclohexane as obtained in step (iii) is a solid, wherein said solid is not subjected to a purification step by recrystallization, i.e. wherein said solid is not transferred to a dissolved condition and precipitates or is precipitated from said dissolved condition to form the purified compound.

In another aspect, the invention also relates to a method of preparing 1-amino-1,3,3,5,5-pentamethylcyclohexane or a pharmaceutically acceptable salt thereof, comprising step (iii):

(iii) reacting 1-hydroxy-1,3,3,5,5-pentamethylcyclohexane with chloroacetonitrile in the presence of an acid, wherein 1-hydroxy-1,3,3,5,5-pentamethylcyclohexane is reacted in step (iii) as obtained in the reaction of a methylmagnesium halide with 3,3,5,5-tetramethylcyclohexanone without having been subjected to a purification step of distillation or chromatography.

For the purpose of this disclosure, the term "pharmaceutically acceptable salts" refers to salts of neramexane that are physiologically tolerable and do not typically produce untoward reactions when administered to a mammal (e.g., human). Typically, the term "pharmaceutically acceptable salt" means approved by a regulatory agency of the Federal or a state government or listed in the U.S. Pharmacopeia or other generally recognized pharmacopeia for use in mammals, and more particularly in humans.

Conversion of 1-amino-1,3,3,5,5-pentamethylcyclohexane to a pharmaceutically acceptable salt thereof is accomplished in conventional fashion by admixture of the base with at least one molecular equivalent of a selected acid in an inert organic solvent. Isolation of the salt is carried out by techniques known to the art such as inducing precipitation with a non-polar solvent (e.g. ether) in which the salt has limited solubility. The nature of the salt is not critical, provided that it is non-toxic and does not substantially interfere with the desired pharmacological activity.

Examples of pharmaceutically acceptable salts are those formed with hydrochloric, hydrobromic, methanesulfonic, acetic, succinic, maleic, citric acid, and related acids.

Further pharmaceutically acceptable salts include, but are not limited to, acid addition salts, such as those made with hydroiodic, perchloric, sulfuric, nitric, phosphoric, propionic, glycolic, lactic, pyruvic, malonic, fumaric, tartaric, benzoic, carbonic, cinnamic, mandelic, ethanesulfonic, hydroxyethanesulfonic, benezenesulfonic, p-toluene sulfonic, cyclohexanesulfamic, salicyclic, p-aminosalicyclic, 2-phenoxybenzoic, and 2-acetoxybenzoic acid.

Within said method of preparing 1-amino-1,3,3,5,5-pentamethylcyclohexane, step (iii) is performed according to any one of the embodiments as defined above.

The method according to the invention allows the omission of complex cleaning steps of the compounds prepared according to steps (ii) and (iii) such as distillation or recrystallization or chromatography, which commonly result in product loss. The yield for step (ii) is 95% in the Grignard reaction (see Example 1) and 94% for step (iii) in the Ritter reaction (see Example 2). Thus, the overall yield over two steps is approx. 88%. The corresponding yield in the reaction sequence as disclosed in the Background section is approx. 73% (85% for the Grignard reaction and 86% for the Ritter reaction).

Since the compound prepared according to step (iii) may be employed in a non-purified form in the next reaction step (iv) of the sequence of preparing Neramexane or a pharmaceutically acceptable salt thereof as referenced in the Background section, the novel simplified method may be performed on an advantageous economical industrial scale.

EXAMPLES

Example 1

A mixture of 153 g 3,3,5,5-tetramethylcyclohexanone and 153 g tetrahydrofurane is added by dropping to a stirred mixture of 93 g methylmagnesium chloride and 372 g tetrahydrofurane. The dropping rate is selected such that the temperature of the mixture can be kept between 5 and 15° C. After the addition is terminated, the mixture is stirred for 60 minutes. Subsequent, diluted hydrochloric acid is added to decompose an excess of methylmagnesium chloride, and to decompose basic magnesium compounds. The mixture is extracted twice with petroleum ether. The extracts are combined and the solvent is distilled off. The yield of crude 1-hydroxy-1,3,3,5,5-pentamethylcyclohexane is quantitative (170 g). The content of target compound in the crude product is about 95% by weight as determined by gas-liquid chromatography.

Example 2

294 g concentrated sulphuric acid are dropped to a stirred mixture of crude 170 g 1-hydroxy-1,3,3,5,5-pentamethylcyclohexane as obtained in Example 1, 150 g chloroacetonitrile and 320 g glacial acetic acid. The dropping rate is selected such that the temperature of the reaction mixture can be kept between 5 and 10° C. After the dropping is terminated, the mixture is stirred for another 60 minutes. Subsequently, the mixture is poured onto a mixture of ice and water. The precipitating target compound 1-chloroacetamido-1,3,3,5,5-pentamethylcyclohexane is separated off by filtration. After drying, 230 g target compound 1-chloroacetamido-1,3,3,5,5-pentamethylcyclohexane are obtained. The yield is nearly quantitative (94% by weight).

The invention claimed is:

1. A method of preparing 1-chloroacetamido-1,3,3,5,5-pentamethylcyclohexane comprising step (iii):
   (iii) reacting 1-hydroxy-1,3,3,5,5-pentamethylcyclohexane with chloroacetonitrile in the presence of an acid, wherein 1-hydroxy-1,3,3,5,5-pentamethylcyclohexane is reacted in step (iii) as obtained via reaction of a methylmagnesium halide with 3,3,5,5-tetramethylcyclohexanone without having been subjected to a purification step.

2. The method according to claim 1, comprising prior to step (iii) step (ii):
   (ii) converting 3,3,5,5-tetramethylcyclohexanone to 1-hydroxy-1,3,3,5,5-pentamethylcyclohexane in the presence of a methylmagnesium halide.

3. The method according to claim 1, wherein the methylmagnesium halide is methylmagnesium chloride.

4. The method according to claim 1, wherein the non-purified 1-hydroxy-1,3,3,5,5-pentamethylcyclohexane comprises 1-hydroxy-1,3,3,5,5-pentamethylcyclohexane in an amount ranging from 85 to 98% by weight.

5. The method according to claim 1, wherein the acid is selected from the group consisting of sulphuric acid, nitric acid, phosphorus acid, acetic acid, and mixtures thereof.

6. The method according to claim 1, wherein sulphuric acid is added to a mixture of 1-hydroxy-1,3,3,5,5-pentamethylcyclohexane, chloroacetonitrile and acetic acid.

7. The method according to claim 1, wherein 1-hydroxy-1,3,3,5,5-pentamethylcyclohexane and acetic acid are provided in a weight ratio of from 1:1.5 to 1:2.5; and, per molar equivalent 1-hydroxy-1,3,3,5,5-pentamethylcyclohexane 1.5 to 2.5 molar equivalents chloroacetonitrile and 2.5 to 3.5 molar equivalents sulphuric acid are employed.

8. The method according to claim 1, wherein in step (iii) the temperature is kept in a range of from 0° C. to 30° C.

9. The method according to claim 1, wherein 1-chloroacetamido-1,3,3,5,5-pentamethylcyclohexane as obtained in step (iii) is not subjected to a purification step.

10. A method of preparing 1-amino-1,3,3,5,5-pentamethylcyclohexane or a pharmaceutically acceptable salt thereof, comprising step (iii):
   (iii) reacting 1-hydroxy-1,3,3,5,5-pentamethylcyclohexane with chloroacetonitrile in the presence of an acid, wherein 1-hydroxy-1,3,3,5,5-pentamethylcyclohexane is reacted in step (iii) as obtained in the reaction of a methylmagnesium halide with 3,3,5,5-tetramethylcyclohexanone without having been subjected to a purification step.

11. The method according to claim 10, comprising prior to step (iii) step (ii):
   (ii) converting 3,3,5,5-tetramethylcyclohexanone to 1-hydroxy-1,3,3,5,5-pentamethylcyclohexane in the presence of a methylmagnesium halide.

12. The method according to claim 10, wherein the methylmagnesium halide is methylmagnesium chloride.

13. The method according to claim 10, wherein the non-purified 1-hydroxy-1,3,3,5,5-pentamethylcyclohexane comprises 1-hydroxy-1,3,3,5,5-pentamethylcyclohexane in an amount ranging from 85 to 98% by weight.

14. The method according to claim 10, wherein the acid is selected from the group consisting of sulphuric acid, nitric acid, phosphorus acid, acetic acid, and mixtures thereof.

15. The method according to claim 10, wherein sulphuric acid is added to a mixture of 1-hydroxy-1,3,3,5,5-pentamethylcyclohexane, chloroacetonitrile and acetic acid.

16. The method according to claim 10, wherein 1-hydroxy-1,3,3,5,5-pentamethylcyclohexane and acetic acid are provided in a weight ratio of from 1:1.5 to 1:2.5; and, per molar equivalent 1-hydroxy-1,3,3,5,5-pentamethylcyclohexane 1.5 to 2.5 molar equivalents chloroacetonitrile and 2.5 to 3.5 molar equivalents sulphuric acid are employed.

17. The method according to claim 10, wherein in step (iii) the temperature is kept in a range of from 0° C. to 30° C.

18. The method according to claim 10, wherein 1-chloroacetamido-1,3,3,5,5-pentamethylcyclohexane as obtained in step (iii) is not subjected to a purification step.

19. The method according to claim 10, where the pharmaceutically acceptable salt is formed by reaction of 1-amino-1,3,3,5,5,-pentamethylcyclohexane with hydrochloric acid or methanesulfonic acid.

* * * * *

UNITED STATES PATENT AND TRADEMARK OFFICE
CERTIFICATE OF CORRECTION

| | | |
|---|---|---|
| PATENT NO. | : 8,759,581 B2 | Page 1 of 1 |
| APPLICATION NO. | : 13/379449 | |
| DATED | : June 24, 2014 | |
| INVENTOR(S) | : Herbert Koller and Michael Pyerin | |

It is certified that error appears in the above-identified patent and that said Letters Patent is hereby corrected as shown below:

Title Page, item [75] Inventor city: "Vienna" should be --Wien--

Title Page, below item [56] References Cited, Foreign Patent Documents: "2007-308480" should be --2007-308460--

Signed and Sealed this
Ninth Day of September, 2014

Michelle K. Lee
*Deputy Director of the United States Patent and Trademark Office*